(12) United States Patent
Kapoor et al.

(10) Patent No.: US 9,700,284 B2
(45) Date of Patent: Jul. 11, 2017

(54) THREE-DIMENSIONAL ULTRASOUND RECONSTRUCTION WITH CONFIDENCE INFORMATION

(71) Applicant: Siemens Medical Solutions USA, Inc., Malvern, PA (US)

(72) Inventors: Ankur Kapoor, Plainsboro, NJ (US); Christian Schulte zu Berge, Munich (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 180 days.

(21) Appl. No.: 14/539,095

(22) Filed: Nov. 12, 2014

(65) Prior Publication Data

US 2015/0133784 A1    May 14, 2015

Related U.S. Application Data (60) Provisional application No. 61/903,551, filed on Nov. 13, 2013.

(51) Int. Cl.
*A61B 8/00* (2006.01)
*A61B 8/08* (2006.01)

(52) U.S. Cl.
CPC .......... *A61B 8/483* (2013.01); *A61B 8/4254* (2013.01); *A61B 8/5246* (2013.01); *A61B 8/0858* (2013.01); *A61B 8/5207* (2013.01)

(58) Field of Classification Search
CPC .. A61B 8/00; A61B 8/08; A61B 8/463; A61B 8/14
See application file for complete search history.

(56) References Cited

U.S. PATENT DOCUMENTS

| | | | |
|---|---|---|---|
| 6,438,401 B1 * | 8/2002 | Cheng | A61B 8/0833 128/898 |
| 7,912,528 B2 * | 3/2011 | Krishnan | G06F 19/345 382/128 |

(Continued)

FOREIGN PATENT DOCUMENTS

| | | |
|---|---|---|
| WO | WO9811823 A1 | 3/1998 |
| WO | WO9825509 A2 | 6/1998 |
| WO | WO2006127142 A2 | 11/2006 |

OTHER PUBLICATIONS

Solberg, O.V., et al., "Freehand 3d ultrasound reconstruction algorithms—a review," Ultrasound in Medicine & Biology, 33(7), pp. 991-1009, 2007.

(Continued)

*Primary Examiner* — Joel Lamprecht (57) ABSTRACT

For simpler scanning in 3D ultrasound imaging, free hand 3D ultrasound imaging is used. Various registration techniques, such as filtering of position signals based on density of scanning and/or counteracting depth deformation due to pressure, may be used for aligning frames relative to each other in 3D space. To deal with curvature of the skin surface resulting in different frames of data representing the same locations, the frames are grouped by orientation. Data representing the same locations in frames of the same or similar orientation are combined. Frame groups of different orientations but of a same sweep of the transducer along the skin are combined into a volume. Volumes from different sweeps are combined. For combining data representing a same location, the values are weighted based on the likelihoods of ultrasound values representing different locations being accurate or correct.

16 Claims, 4 Drawing Sheets

(56) References Cited

U.S. PATENT DOCUMENTS

| | | | |
|---|---|---|---|
| 2005/0119568 A1* | 6/2005 | Salcudean | A61B 8/08 600/437 |
| 2007/0232908 A1* | 10/2007 | Wang | A61B 8/08 600/437 |
| 2010/0198068 A1 | 8/2010 | Rivaz et al. | |
| 2012/0165672 A1* | 6/2012 | Hill | A61B 8/0883 600/443 |

OTHER PUBLICATIONS

Wein, W., et al., "Backward-warping ultrasound reconstruction for improving diagnostic value and registration," Medical Image Computing and Computer-Assisted Intervention—MICCAI 2006, vol. 4191 of Lecture Notes in Computer Science, Springer Berlin Heidelberg, pp. 750-757, 2006.

Rohling, R., et al., "A comparison of freehand three-dimensional ultrasound reconstruction techniques," Medical Image Analysis 3(4), pp. 339-359, 1999.

Sanches, J.M., et al., "A multiscale algorithm for three-dimensional free-hand ultrasound," Ultrasound in Medicine & Biology 28(8), pp. 1029-1040, 2002.

Klein T., et al., "Modeling of multi-view 3d freehand radio frequency ultrasound," Medical Image Computing and Computer-Assisted Intervention—MICCAI 2012, vol. 7510 of Lecture Notes in Computer Science, Springer Berlin Heidelberg, pp. 422-429, 2012.

Treece, G., et al., "Correction of probe pressure artifacts in freehand 3d ultrasound," Medical Image Analysis 6(3), pp. 199-214, 2002.

Housden, R.J., et al., "Sensorless reconstruction of unconstrained freehand 3d ultrasound data," Ultrasound in Medicine & Biology 33(3), pp. 408-419, 2007.

Karamalis, A., et al., "Ultrasound confidence maps using random walks," Medical Image Analysis 16(6), pp. 1101-1112, 2012.

Shepard, D., "A two-dimensional interpolation function for irregularly-spaced data," In: Proceedings of the 1968 23rd ACM national conference, ACM '68, New York, NY, USA, ACM, pp. 517-524, 1968.

Wein, W., et al., "Image-based method for in-vivo freehand ultrasound calibration," In SPIE Medical Imaging 2008, San Diego, 2008.

Comaniciu, D., et al., "Robust real-time myocardial border tracking for echocardiography: an information fusion approach," IEEE Transactions on Medical Imaging 23(7), pp. 849-860, 2004.

* cited by examiner

THREE-DIMENSIONAL ULTRASOUND RECONSTRUCTION WITH CONFIDENCE INFORMATION

RELATED APPLICATIONS

The present patent document claims the benefit of the filing date under 35 U.S.C. §119(e) of Provisional U.S. Patent Application Ser. No. 61/903,551, filed Nov. 13, 2013, which is hereby incorporated by reference.

BACKGROUND

The present embodiments relate to medical imaging and, in particular, to three-dimensional (3D) ultrasound imaging.

3D ultrasound imaging has many applications, such as cardiac or radiological imaging. For example, one possible application is musculoskeletal (MSK) applications, where traditional imaging modalities are X-Ray and magnetic resonance (MR) imaging. X-Ray not only uses ionizing radiation but also has very weak tissue contrast, and MR imaging is far from real-time and additionally restricts the anatomy to be in a position that might not be suited well for diagnostics. 3D ultrasound scans in real-time and has good tissue contrast, but may have undesired variability between patients and users. Due to the dynamics and high complexity of the ultrasound image formation being dependent on incident angle, probe pressure, patient positioning and patient breathing cycle, ultrasound may yield different information (i.e. image intensities) for the same point within the anatomy if scanned at a different time or from a different perspective.

BRIEF SUMMARY

By way of introduction, the preferred embodiments described below include methods, computer readable media, and systems for 3D ultrasound imaging. For simpler scanning, free hand 3D ultrasound imaging is used. Various registration techniques, such as filtering of position signals based on density of scanning and/or counteracting depth deformation due to pressure, may be used for aligning frames relative to each other in 3D space. To deal with curvature of the skin surface resulting in different frames of data representing the same locations, the frames are grouped by orientation. Data representing the same locations in frames of the same or similar orientation are combined. Frame groups of different orientations but of a same sweep of the transducer along the skin are combined into a volume. Volumes from different sweeps are combined. The combinations may use likelihood information. The likelihood of ultrasound values representing different locations being accurate or correct is used in 3D ultrasound imaging. For combining data representing a same location, the values to be combined are weighted based, at least in part, on the likelihoods. Orientation-based combination, likelihood combination, and/or registration approaches may be used alone or in combinations.

In a first aspect, a method is provided for three-dimensional ultrasound imaging. An ultrasound system including a transducer acquires first and second ultrasound data representing a same volume of a patient. A processor assigns confidence values as a function of location within the volume to the first and second ultrasound data. The processor combines the first and second ultrasound data representing the same locations within the volume. The combining is a function of the confidence values for the locations. An image is generated on a display using results of the combining. The image represents the volume of the patient.

In a second aspect, a non-transitory computer readable storage medium has stored therein data representing instructions executable by a programmed processor for three-dimensional ultrasound imaging. The storage medium includes instructions for obtaining data representing a volume of a patient from a transducer moving over a curved surface of the patient, the data being in frames representing locations and having at least two different orientations relative to the volume; dividing the data into a first set of the frames having a first orientation of the at least two different orientations and a second set of the frames having a second orientation of the at least two different orientations; first compounding the data of the frames of the first set where the data represents the same locations; second compounding the data of the frames of the second set where the data represents the same locations; and third compounding the data of the first set with the data of the second set where the data represents the same locations.

In a third aspect, a system is provided for three-dimensional ultrasound imaging. An ultrasound system is configured to use a transducer for scanning in three-dimensions where different data represents the same locations. The ultrasound system includes a processor configured to label the different data with respective indications of reliability and configured to combine the different data for each of the same locations as a function of respective indications. A display is configured to display an image from a three-dimensional reconstruction from the combined different data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

For freehand 3D ultrasound, a transducer for two-dimensional scanning is equipped with 6 degree-of-freedom tracking hardware to reconstruct a 3D volume of the target anatomy. Freehand scanning allows the clinician to examine the anatomy in almost any arbitrary position while showing both tissue and bone interfaces, which makes 3D freehand ultrasound a promising modality for MSK and other applications such as prostate or abdominal ultrasound.

Since tracking hardware has a limited (e.g., for high-quality reconstruction not sufficient) accuracy, more accurate orientation and position information is extracted based on the image content. Accurate 3D reconstruction is provided by handling ambiguities during the spatial compounding process. The clinician scans the target anatomy in a painting-like motion not being restricted to unidirectional sweeps. To achieve a high-quality 3D reconstruction, the acquired 2D ultrasound images are passed through a processing pipeline recovering orientation and position errors present due to the limited tracking accuracy, and grouping the frames into sequences with uniform orientation. The 2D frames are transformed into 3D space using the orientation and position information, and their image information is compounded into a 3D volume. Possible ambiguities due to multiple scans of the same anatomy from different angles are resolved by incorporating uncertainty information into the compounding process.

For real-time applications, the compounding may be performed incrementally for each group of ultrasound frames to allow for a continuous update and refinement of the reconstructed volume during the acquisition. Furthermore, the uncertainty information may be presented to the clinician to assist in determining regions needing further examination.

Various approaches may be used to improve the 3D ultrasound imaging. An initialization phase or other indication where the clinician defines the extent and orientation of the volume to be reconstructed is used. The volume extent is defined by a painting motion or transducer movement. Freehand 3D ultrasound reconstruction allows arbitrary acquisition trajectories. Adaptive filtering of tracking data based on frame sampling density may avoid jitter in the tracking. Grouping of the frames within a sweep into continuous groups of homogeneous orientation may perform well with motion of the transducer over curved surfaces. By subdividing the ultrasound frames into a grid of patches for frame-to-frame spatial registration, pressure compensation is provided. Patch-wise inter-frame registration over a weighted window of adjacent frames removes artifacts from variance in pressure on the skin over time. For more efficient combination, a two-step compounding technique first samples (scan line voxelization) frames into an intermediate representation then performs backward compounding. For fusion of frames/sweeps from multiple angles, an uncertainty measure is included. Presenting confidence information in a reconstructed volume to a clinician may feedback acquisition quality information.

Figure 1:
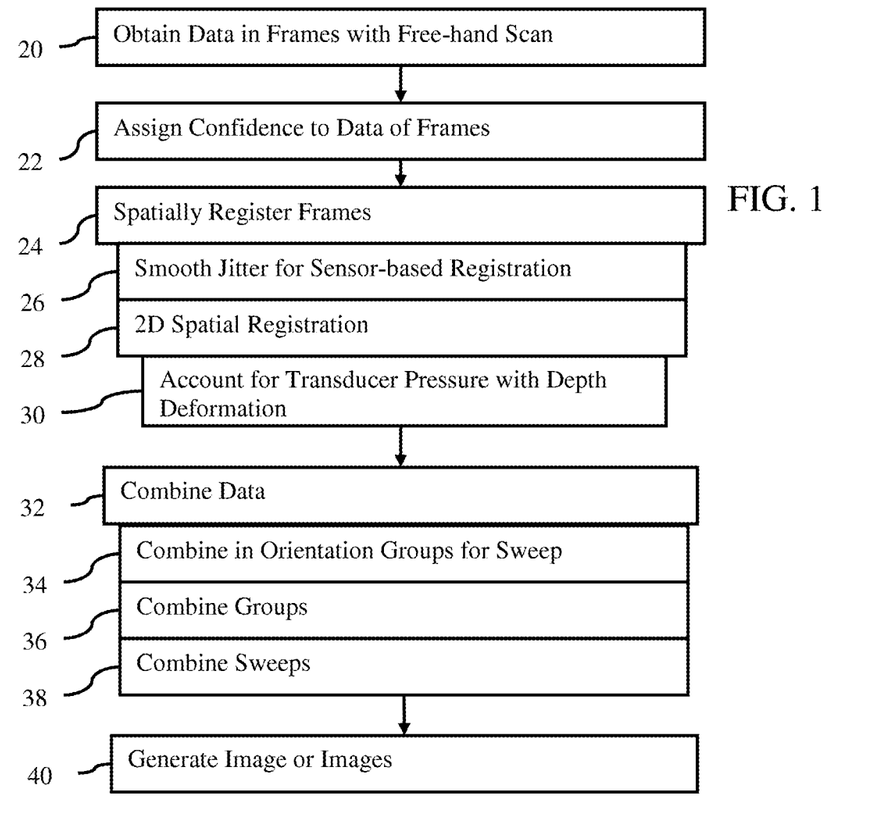
FIG. 1 is a flow chart diagram of one embodiment of a method for 3D ultrasound imaging.

FIG. 1 shows one embodiment of a method for 3D ultrasound imaging. The method includes registration using smoothing of sensor signals, registration accounting for depth deformation, combining data in orientation-based groups, and/or combining data using confidence weighting. Any combination of these features may be used. In one embodiment, all of the features are used.

Additional, different, or fewer acts may be performed. For example, act 22 is not performed where confidence is not used. As another example, acts 26, 28, and/or 30 are not performed. In yet another example, acts 34, 36, and/or 28 are not performed. In other examples, additional registration, compounding, and/or imaging are provided. The confidence information may be used to generate an image modulated by or representing the confidence. The user may be guided by the confidence information for selecting where to continue to scan.

The method is implemented in the order shown or a different order. For example, acts 28 and 30 may be performed before act 26. As another example, act 38 may be performed prior to act 36, such as combining groups from different sweeps for a same orientation before combining the groups of different orientations. In yet another example, act 22 is performed any time before one of acts 32-38.

The acts are performed in real-time. In freehand operation, the clinician slides the transducer along a skin surface of the patient. The path along the skin may be in one direction or may curve. The angle of the transducer relative to the skin surface may stay constant or may vary. The orientation of the scanning may change relative to the patient due to the skin surface curving. For example, the scan is over a shoulder or a stomach of a pregnant lady. The clinician may reverse the sweep of the transducer, such as sliding the transducer back and forth in a painting motion with or without a change in orientation relative to the skin surface. The transducer may be rotated about an axis orthogonal to the skin surface. Freehand scanning allows for various motions or combinations of motion of the transducer. In alternative embodiments, a fixed or three-dimensional scanning transducer is used.

During real-time scanning, images using the gathered scan data may be generated to assist in gathering further information. Images are generated during the scanning (e.g., less than 3 second delay from acquisition to use of the data in an image) so that the clinician may identify regions needing additional focus or data. The transducer is moved to scan the regions. In alternative embodiments, the imaging is generated after the scanning, such as not in real-time with the scanning. The acts are performed off-line, such as for planning or result determination.

The acts are performed by a transducer, ultrasound imaging system, and/or processor. The user moves the transducer over the patient. While moving, the ultrasound system obtains scan data representing the patient in act 20 with the transducer. The processor performs acts 22-38, operating on data representing the patient to transform the representation of the patient into a higher quality image of the patient. The transformation results in less noise and inaccuracy in the imaging. A display presents the image to the clinician or others. In one embodiment, the system of FIG. 14 performs the method. Other devices may perform one or more of the acts.

In act 20, data representing a patient is obtained. The data is acquired by scanning the patient. An ultrasound system scans the patient by generating acoustic energy with a transducer and receiving echoes. Any scanning sequence or approach may be used, such as a linear, Vector® or sector scan format of scan lines. The echoes are received by the transducer and converted into electrical signals. The electrical signals are processed to detect intensity (e.g., B-mode), tissue strain, power Doppler, contrast, tissue harmonics, elastic modulus, relaxation time, other tissue property, or other scalar information. For a given scan, transmission and reception are performed for a plurality of scan lines lying in a plane. A frame of data representing the plane is acquired. As the transducer is moved, other frames representing different planes are acquired. Due to the speed of movement and/or change in angle, some frames may represent one or more locations of other frames.

In an alternative embodiment, the data is acquired by loading from memory. Data from a previously performed scan of the patient is stored in a memory, such as a picture archiving and communications system (PACS) database. The data is selected from the database. The data may be obtained by transfer, such as over a network or on a portable memory device.

The data represents a volume. A three-dimensional region is represented. For data converted to a 3D grid, the data is formatted in an N×M×O grid where N, M and O are integers greater than one. The frames of data may not align with the 3D grid, so the data represents a plurality of planes distributed in the volume. For each frame, the data represents samples along an acoustic grid (e.g., beamform samples along scan lines in the scan format) or scan converted data in a 2D Cartesian coordinate system for the frame. Each frame represents 2D, but the frames together represent locations distributed in three dimensions.

Due to overlap, orientation change, or rescanning a same location at different times (e.g., sweeping the transducer back and forth), data of one frame may represent a same location as data of another frame. A same volume may be represented by different sets of ultrasound data. A given set of data representing a volume may extend beyond the same volume, such as representing a location or locations different than for another volume.

The volume is a 3D region of the patient. Data may represent a same volume by representing one or more locations of the 3D region. For example, the same volume is represented by different ultrasound data due to sweeping to scan the 3D region or an overlapping part of the 3D region twice or more. As another example, the same volume is represented by different ultrasound data due to scanning from different orientations in a single sweep along one direction. As the transducer moves over a curved surface, the orientation changes so that the same locations are scanned from different directions. In yet another example, the sweep occurs slowly, so data representing the same locations in the volume are acquired due to the relatively rapid frame rate even if part of a same sweep and having a same orientation.

A sensor is attached to the transducer to track motion. For example, an electric field or electromagnetic sensor is used for tracking the position of the transducer relative to a reference sensor or antenna. In alternative embodiment, other types of sensors for tracking position and orientation of the transducer are used, such as an optical sensor or camera. The sensor indicates position and/or motion of the transducer over any number of degrees of freedom, such as over six degrees of freedom (e.g., three translation and three rotation). The position and orientation of the transducer relative to a reference point are indicated by signals from the sensor.

Since the patient may move during an examination, another sensor may be used to determine patient motion. The patient motion may be removed from the motion of the transducer to determine the motion of the transducer relative to the patient.

In one embodiment, the acquisition includes inputting an indication of an extent of the volume in the patient and/or range of positions of the transducer to scan the volume. The extent is derived from the tracking as the transducer scans. Alternatively, the extent is defined in a calibration or initial phase prior to scanning. For example, in an initialization phase, the clinician defines the extent of the 3D volume to be reconstructed by moving the transducer to the borders of the target volume. During this initialization, the system records the tracking data and computes the volume extent based on the probe movement. Furthermore, the general orientation of the scan (i.e., direction in which the transducer is pointing with respect to the anatomy) is defined during the initialization phase.

After any calibration or initialization, the clinician starts the acquisition, such as by pushing a button. The ultrasound system generates and records the ultrasound data together with the tracking data from the sensor or sensors. This acquired data is then sent to the processing and compounding pipeline, where the 2D images are transformed into 3D space incrementally updating the compounded volume by performing the other acts of the method of FIG. 1. The resulting 3D imaging may be visualized to the clinician. While acquiring the data, the clinician is not restricted to perform the sweep in a specific manner. Instead, the clinician may perform the acquisition in an arbitrary (e.g. painting-like) motion and monitor the progress of the reconstruction on the system.

In act 22, confidence values are assigned to the data. The confidence values represent the quality of the ultrasound data. Each ultrasound value in a frame of data has an accuracy, quality, likelihood, or level of uncertainty regarding the accuracy of the representation of the acoustic response of the location. Confidence values are assigned to respective ultrasound values for each frame. Different or the same confidence values are assigned for the different locations or values in a frame of data. Due to various factors, different locations represented by a frame may have different confidence values. Accordingly, different locations within a volume have different confidence values. The same location in the volume may have the same or different confidence values in different frames.

The uncertainty is inherent in every frame of data and dependent on various ultrasound phenomena, such as refection, shadowing, and/or attenuation. Uncertainty information may be computed using confidence maps. Any approach for computing per-pixel uncertainty information based on ultrasound physics may be applied.

A processor assigns the confidence values. Using a look-up table, image processing, filtering, classification, or other process, the processor determines the confidence values to assign. The confidence values may be assigned as uncertainty, quality, likelihood, or probability values.

In one embodiment, the confidence values are assigned as a function of the scan format and/or depth. For example, deeper locations may have less confidence and shallower more. As another example, locations at the edge of a scan format may have less confidence due to a reduced aperture. The width of the field of view may provide for different levels of confidence. In other examples, the scan format may result in different confidences for different locations. The location of an apex in a given sector or vector scan format may determine the confidence values being assigned.

The ultrasound image geometry is determined from settings of the ultrasound system. Alternatively, the ultrasound image geometry is determined by image processing of the output image or frame of data.

In another embodiment, the confidence values are assigned as a function of structure, object, or information detected in the volume. For example, the scanning may be performed for a particular body part or region, such as through the clinician selecting a scan application (e.g., selecting MSK). Based on this expected structure, confidence values are assigned. Different confidence values for the same locations with a same scan format may result due to scanning different targets. In another example, a machine learnt classifier or other image processing is applied to identify specific structures or artifacts or is applied to assign values based on structure or artifacts represented in the frame of data. For example, a bone or denser region is detected. Since bone or dense tissue may cause shadowing, a lower confidence value is assigned to any locations along scan lines separated from the transducer by the bone or dense region.

In yet another embodiment, the confidence values are assigned as a function of both (1) scan format and depth and (2) structure represented in the volume. The confidence values are computed based on current acquisition parameters, image content, and/or other parameters. In one approach, a look-up table is used to assign initial confidence values based on scan format and depth. These confidence values are then adjusted based on structure or artifacts represented in the volume. In other approaches, the structure is used for initial assignment, and scan format and depth are used to adjust. In an alternative embodiment, any parameters (e.g., scan format, depth, and structure) are used as inputs to a classifier that outputs a confidence value for a given location.

Figure 2:
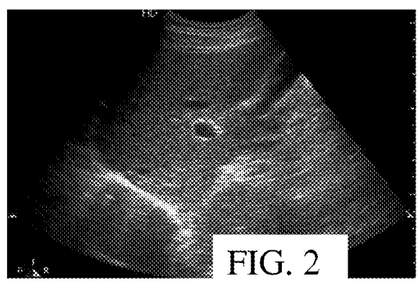
FIG. 2 illustrates an example ultrasound image for a plane.
Figure 3:
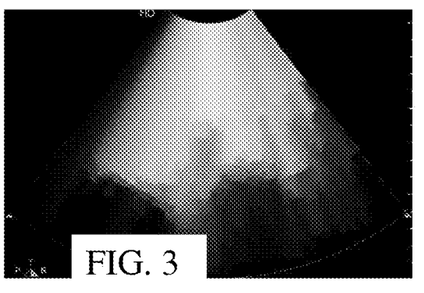
FIG. 3 shows an example confidence map for the image of FIG. 2.

FIG. 2 shows a B-mode image of a liver generated from a frame of ultrasound data. FIG. 3 shows the confidence map with confidence values assigned for the frame of data used for FIG. 2. Brighter regions depict higher confidence or less uncertainty, and darker region depict lesser confidence or higher uncertainty. Generally, shallower regions have greater confidence than deeper regions. In FIG. 2, the lower left portion shows a bright "bar" shaped region corresponding to higher density. The resulting shadowing causes the locations beyond the bright region to have lower confidence values. The confidence values are assigned for each frame of data.

To simplify processing for real-time use, confidence values may be assigned to down sampled frames of data. The ultrasound scan lines are resampled into a standard 2D array of intensity values if needed. For example, a frame of data representing a sector or vector scan is resampled to resemble a linear scan, such as by formatting to provide the values along scan lines. The linear scan format in the acoustic domain is used as the standard. Other standards may be used. A median-filtered or other down sampling by a factor of 4 or other number reduces noise and confidence map computation time. The computed uncertainty information is stored in a contiguous buffer or other memory together with the frames of data. To upscale confidence values to the original frame dimensions, bilinear filtering or other interpolation is performed as needed.

In act 24, the frames are spatially registered. The spatial registration is relative to the volume and/or other frames. The frames are spatially registered with each other so that the proper or actual position of the planes represented by the frames is located in the volume.

The registration uses calibration of the tracking sensor, patient registration, and/or transducer tracking registration. The calibration represents an adjustment or correction to relate signals from the tracking sensor to actual position. The patient registration represents motion of the patient altering the tracking. The tracking registration represents the position and orientation of the transducer at the time or period during which a given frame of data is acquired by scanning.

The transformation of a point $v_f$ in a 2D ultrasound frame i into 3D world coordinates is given by:

$$v_w = T_P T_{T_i} T_C \cdot v_f$$

where $T_P$ is the patient registration matrix, $T_{T_i}$ is the transducer tracking matrix for frame i and $T_C$ is the transducer calibration matrix. Tracking methods have limited accuracy and thus may be post-processed to yield high-quality 3D reconstructions. As a result, other registration may be performed.

In act 26, the transform based on tracking signals is altered or a further transformation matrix is included to increase the accuracy of the tracking signals. The locations from planes represented by the frames are transformed in 3D space using the signals from the sensor on the transducer. These signals are filtered to increase accuracy or remove noise. For example, the signals are low pass filtered. The sensors of position as a function of time are temporally or spatially filtered. Any low pass filtering may be used.

In one embodiment, the filtering adapts to the positions or motion sensed by the sensors. The kernel size or other filtering characteristic is a function of the density of the scan planes of the frames. To compensate for high-frequency jitter artifacts within the tracking signal, adaptive low-pass filtering has a local kernel size dependent on the ultrasound frame sampling rate. The speed of frame acquisition (e.g., frame rate) and the change in position or velocity of the transducer indicates the density (e.g., how close adjacent frame are) of the planes represented by the frames in the volume. Any temporal window for measuring density may be used. Given a constant frame rate, faster motion of the transducer provides a less density and slower motion of the transducer provides a greater density. Lower density maps to a larger kernel size using a linear or non-linear function.

The filtering of the sensor signals may distort the planes or locations represented by the frames. A transform may be used to account for the deformation due to smoothing. Applying the filter to the world coordinates of the four corners of each frame, two sets of corners result. One set of corners is the original coordinates indicated before filtering. The other set of corners are the coordinates indicated after filtering. Normals of the planes defined by these two sets of coordinates are calculated for each frame. The change in the normals defines a smoothing matrix to counter any random noise and/or high frequency errors in the sensor signals (e.g. as electromagnetic interference, hand tremor). A smoothing matrix $T_{S_i}$ is added to the transformation chain to filter translation and rotation, as represented by:

$$v_w = T_{S_i} T_{T_i} T_C \cdot v_f$$

Figure 4:
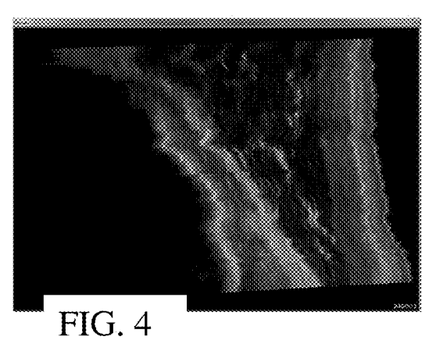
FIG. 4 shows an example reconstructed slice image through a volume without filtering tracking singles from a transducer sensor.
Figure 5:
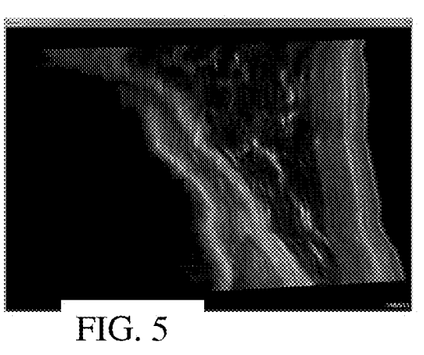
FIG. 5 shows the example reconstructed slice image with filtering of the tracking signals based on scan density.

FIG. 4 shows a sagittal reslice through a compounded volume without filtering. FIG. 5 shows the same sagittal reslice with filtering and application of the smoothing matrix to account for tilt in the planes caused by the filtering. The filtering reduces jitter shown in FIG. 4.

In act 28, another registration may alternatively or additionally be included to refine the relative positioning and orientation of the planes in the volume. As the transducer is moved, frames of data that are generally parallel (e.g., within +/−2 degrees of each other) are acquired. The frames may or may not overlap (e.g., be close enough together that the data from each frame represents, at least in part, a voxel region for a same voxel or voxels). Given the adjacency and similarity, the frames may be registered spatially relative to each other along two dimensions. Since low-frequency errors in the tracking data (e.g. drift due to inaccurate calibration, probe pressure changes or patient movement) may not be resolved by filtering, inter-frame registration is applied as an additional registration in one embodiment.

In act 28, the frames are spatially registered relative to each other. The adjacent frames may be part of a same sweep or different sweeps. Any grouping or windowing may be used based on time of acquisition, orientation, and/or spatial adjacency.

The rotation and/or translation in a two-dimensional plane leading to the greatest similarity measure are found. A pixel or location wise uphill or other type of search is used to find the rotation and translation with the greatest or sufficient similarity. This rotation and translation indicates correct registration.

Any inter-frame two-dimensional measure of similarity may be used. For example, the sum of squares of differences is calculated. In other examples, a correlation, minimum sum of absolute differences, or other measure of similarity is used.

The similarity is measured between pairs of frames. In other embodiments, a window of three or more frames is used so that the registration for a given frame is to more than one other frame. The registration may be weighted, such as weighting spatially and/or temporally closer frames more heavily. In one embodiment, regularization is performed by registering each ultrasound frame to a window W of surrounding frames. Using the window compensates for drift independently of the tracking calibration accuracy. Since the correlation between two ultrasound frames does not only depend on their proximity but also on their orientation to each other, the weights for the frames in W are determined by a combination of a Gaussian kernel of size N and a term C, which describes the orientation-based correlation between two images. For a given reference patch P (e.g., whole frame or part of frame) and an equally sized moving patch $P_0$, the windowed sum of square of the differences SSD (wSSD) is given by:

$$wSSD_{P,P'}(i) = \sum_{\substack{p \in P \\ p' \in P'}} \sum_{n=-N}^{N} C(i, i+N) \cdot e^{\frac{n^2}{2\sigma^2}} \cdot (I_i(p) - I_{i+n}(p'))^2 \quad (1)$$

where i is the index of the reference frame and $I_i(p)$ denotes the image intensity of ultrasound frame i at the position p. The correlation term C(i; j) for frames i and j is defined by the cosine distance of their normals $n_i$; $n_j$ to model the decreasing correlation between frames of increasing orientation difference:

$$C(i, j) := 1 - \frac{2}{\pi} \cdot acos\left(\frac{n_i \cdot n_j}{\|n_i\| \|n_j\|}\right) \quad (2)$$

In one embodiment, the confidence values are used in the registration. Since shadows or other artifacts in ultrasound imaging may vary over time, scan direction, and/or spatial location, registration may be less reliable where the artifacts exist. By weighting the registration so that locations with lower confidence values contribute less to the registration, more accurate registration may be provided.

Using the tracking data as initialization of spatial registration may limit the searching. Since the tracking data provides a good initialization or initial registration, advanced registration optimization techniques, such as pyramids or pre-filtering, are not necessary, but may be used. Sub-pixel and sub-angle accuracy transformation t may be provided. Rather than finding a single offset (e.g., rotation and translation), the offsets for the greatest and adjacent similarities are found. The difference is used for weighted interpolation of the offsets between the two results with maximum correlation. This is represented as follows:

$$t = \left\{ t_r + \frac{d}{2} \frac{c_1 + c_{-1}}{c_0 + c_1} \quad c_{-1} > c_1 \right. \quad (3)$$
$$\left\{ t_r + \frac{d}{2} \frac{c_1 + c_{-1}}{c_0 + c_{-1}} \quad c_{-1} < c_1 \right.$$
$$\left\{ t_r \quad c_{-1} = c_1 \right.$$

where $t_r$ is the transformation with maximum correlation, d the step size, $c_0$ the maximum correlation and $c_{-1}$, $c_1$ the correlations of the two neighbors of the maximum correlation.

Figure 6:
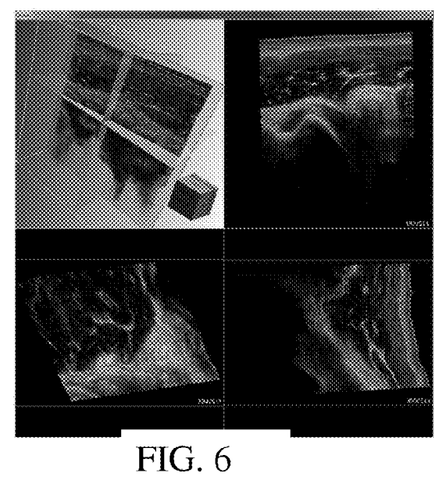
FIG. 6 shows example images with the filtering of FIG. 5 but without inter-frame registration.
Figure 7:
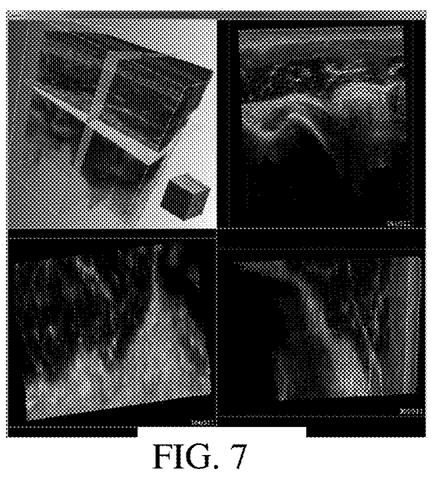
FIG. 7 shows the example images of FIG. 6 with added inter-frame registration.

FIG. 6 shows a volume representing reformatted slices through a volume and the ultrasound images for the three planes without inter-frame registration. FIG. 7 shows the volume and corresponding images for the planes with inter-frame registration. The inter-frame registration provides more accurate images.

In act 30, the inter-frame registration accounts for transducer pressure variation by applying a depth deformation. Different amounts of transducer pressure result in different compression of the tissue in the volume. As a result, a given frame of data represents different tissue than another even if for the same plane and field of view.

Rather than correlation of entire frames of data together, the frames are divided into smaller patches. Patches are independently correlated with one or more adjacent frames with different offsets. The offset with the greatest correlation or correlations are found for each of the patches. Sub-pixel and/or sub-angle interpolation may be used.

Any size patches may be used, such as 9×16 patches of equal size with or without overlap with other patches for the same frame (e.g., a 1.5 overlap factor). A grid of n×m patches (e.g., 20×30 patches) is used. The frame is sub-divided into patches.

For depth-based transformation, one patch or a number of patches along a similar depth are set as the reference or central patch for rigid transformation. The differences in offset of other patches as compared to the reference patch provide a deformation field. For a linear scan format, the deformation field may be constrained by only allowing deformation in depth, as expected from probe pressure. For vector or sector formats, the deformation is in depth but may also contain some axial or lateral deformation. For such vector or sector formats, the deformation field may be constrained along the radial direction. The deformation may be constrained along any dimension. The deformation may be constrained based on the physical form factor of the transducer housing, as the pressure and hence the resultant deformation in the tissue is influenced by the transducer geometry.

In one embodiment, the deformation is calculated as the inverse of the relative offsets by a Banach fix-point iteration. Any number of iterations, such as 16 iterations, may be used. Other calculations of expansion or contraction may be used.

Figure 8:
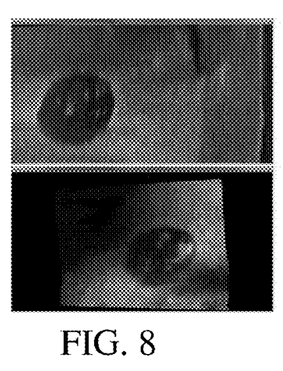
FIGS. 8, 9, and 10 show example images for perpendicular planes without pressure compensation, with pressure compensation using one-dimensional registration, and with pressure compensation using two-dimensional registration, respectively.
Figure 9:
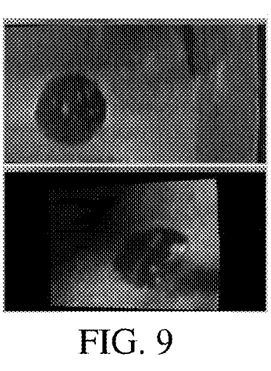
Figure 10:
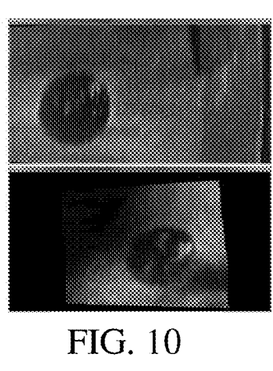

In the presence of pressure artifacts, the inverse deformation to remove the artifacts may increase the image quality. FIGS. 8, 9, and 10 each show two images. The upper image is a sagittal slice or cross-section orthogonal to the depth direction, and the lower image is a coronal slice or along a plane through the transducer, such as being for a plane scanned to provide a given frame of data. FIG. 8 shows a spherical object with no pressure compensation. FIG. 9 shows the same object with pressure compensation using 1×16 patches to restore in the sagittal direction of the upper figure. FIG. 10 shows the same object with pressure compensation using 9×16 patches to restore deformation in the sagittal and coronal directions.

For use with other registrations, the inter-frame translation and rotation are subtracted from the tracking data. The remainder is a registration matrix $R_i$ for frame i to frame i−1. The final registration matrix $T_{R_i}$ for frame i is given by the product of all previous registration matrices:

$$T_{R_i} = R_1 \ldots R_i$$

which is added by matrix multiplication to the frame-to-world transformation chain:

$$v_w = T_{Si} T_P T_B T_C T_{Ri} \cdot v_f$$

Other registrations with fewer, different, or additional transformations may be used. The registration indicates the location of each frame in the 3D space or volume of the patient.

Once registered, frames representing locations in common with other frames are compounded. The ultrasound values representing a given location are determined from all of the frames representing that location. For each location represented by more than one frame of data, the ultrasound values from the frames for that location are combined. Frames may represent a same location due to density of sampling, scanning from different orientations, and/or scanning a region or the volume more than once (e.g., two or more sweeps over part or all of the volume).

As long as the probe movement of an acquisition sweep is restricted to a single direction at a speed relative to the frame rate to avoid overlap and the probe orientation kept perpendicular, none of the frames overlap, which keeps the 3D spatial compounding problem simple. For freehand or other scanning, these conditions may not be met. Compounding from arbitrary sweep trajectories is provided by resolving possible ambiguities where multiple frames intersect.

In act 32, ultrasound data representing the same locations within the volume are combined. A processor averages or weighted averages to combine. In alternative embodiments, a maximum or minimum selection may be used. Other combination functions may be used by the processor.

For combination, the frames may be interpolated to a three-dimensional grid or voxel representation. The voxel size indicates the locations of the frames which intersect with the voxel. The ultrasound values for these intersecting locations are combined. Ultrasound values from adjacent or near locations may be included in the combination in an interpolation. Alternatively, the combination is performed for locations in the frames and then the results of the combination are interpolated to the three-dimensional grid.

The combination is a function of the confidence values for the locations. The confidence values are used as values of a variable in the combination. In one embodiment, the compounding is a weighted combination, such as a weighted average. The weights are based, at least in part, on the confidence values. For combining two or more ultrasound values representing a same location, each ultrasound value is weighted by the respective confidence value for the location. Values associated with higher confidence values are more strongly weighted, and values associated with lower confidence values are more weakly weighted. Where the confidence values are assigned as being in the 0-1 range, the confidence values themselves may be used. Alternatively, the confidence values are mapped to weights using a linear or non-linear function, such as mapping confidence values above a threshold to 1, below another threshold to 0, and between the thresholds to a range of lower weights (e.g., ramp or decay function). In alternative embodiments, the combination is a function of the confidence values in another way, such as using the confidence values to select the function used for combining.

As represented in acts 34, 36, and 38, any one of various combinations may be performed and/or may use confidence values. In one embodiment represented by act 34, the frames are separated into groups associated with a same or similar orientation within a limited spatial extent and compounding is performed within each group. In act 36, the ultrasound values from the groups with overlapping locations are compounded. In act 38, the ultrasound values from different sweeps (transducer scanning the volume a subsequent time) are compounded for overlapping locations. In alternative embodiments, one combination for all ultrasound values per location is performed. Other divisions and compounding stages may be used, such as compounding for orientation groups and then compounding groups and sweeps together (e.g., weighted average).

In act 34, the frames of ultrasound data are divided into groups, and the frames of each group are compounded together. Any division may be used, such as based on time of scanning, location of scanning, and/or orientation of scanning. In one embodiment, the location and orientation of scanning is used. Frames of a same orientation or within +/−X degrees are grouped. X may be any value, such as 3.0 degrees. Within the frames of the same or similar orientation, further grouping or separation may be provided based on location. If the frames are within Y cm of each other measured from the center location in the field of view or by the transducer, then the frames are grouped. Y may be any value, such as 1.0 mm. Y may also depend on the density of frames, the voxel size, or both. Any location grouping may be used.

In one embodiment, a hierarchical clustering identifies tortuous sweep trajectories and regions of overlapping ultrasound frames. The clustering partitions the ultrasound sweep trajectory into parts where the frames have homogeneous orientation without requiring predefinition of the number of clusters. An average group linkage algorithm using cosine distance to the normals of the ultrasound frames (see equation 2) is applied, yielding a set of sub-sweeps of frames meeting the restrictions of being contiguous and uniformly oriented.

Figure 11:
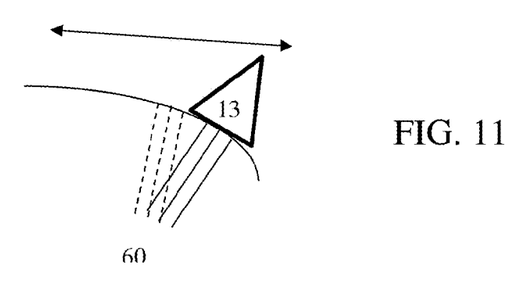
FIG. 11 illustrates a free hand sweep of the transducer along a curved surface resulting in groups of scan planes.

FIG. 11 shows two example groups of contiguous frames (represented by solid line and dashed lines) from a sweep of the transducer in a direction along a curved skin surface. The six frames shown are divided into two groups of frames with the same or similar orientation. Within each group, ultrasound values representing the same location are compounded. Given the same or similar orientation, the compounding may be due to frame density. Multiple frames may represent the same voxels, so are combined. During compounding, each group is handled independently.

In one embodiment, a backward compounding is performed to compute the set S of frame pixels. The weighting function not only considers the distance d of each pixel to the voxel center but also the local confidence C and returns the final voxel intensity Iv and confidence Cv. The compounding is represented as:

$$I_v = \frac{\sum_{i \in S} I_i \cdot d_i^\mu C_i^{2\mu}}{\sum_{i \in S} d_i^{-\mu} C_i^{2\mu}}$$

$$C_v = \max_{i \in S} C_i$$

This backward compounding pass is performed for each location in each group of frames. The results are written to a 3D volume storing intensities and local confidence values.

In act 36, the groups are compounded. Within a sweep along the skin surface, the groups with different orientations and/or locations are combined. For each voxel in the 3D space or grid, the ultrasound values from different groups representing the voxel are weighted and compounded. In one embodiment, the weights are again a function of the confidence for the ultrasound value. Distance may or may not be used. The confidence value from the compounding within the group is the maximum of the confidences. These maximum confidences are used as weights for the respective ultrasound values of the groups. Each ultrasound value is weighted and the results summed. The compounding fuses multiple groups of frames into the reconstructed volume.

For real-time applications, the fusing is performed directly in place, and the compounded volume is taken as accumulation in a buffer, where the reconstructed groups are incrementally added using a blending technique updating both intensities and local confidence. Given the voxel intensity $I_{i-1}$ and confidence $C_{i-1}$ of the previous runs and $I_v$, $C_v$ from the current group, the new intensity $I_i$ and confidence $C_i$ are represented as:

$$I_i = \frac{C_{i-1} I_{i-1} + C_v I_v}{C_{i-1} + C_v}$$

$$C_i = \max(C_v, C_{i-1})$$

While being dependent on the ordering of the compounding of the different clusters, this technique offers a low complexity and memory footprint. Other approaches may be used.

By compounding the groups together, a sweep volume is formed. The groups represent the volume of the patient. For the volume, voxels having an assigned ultrasound value and confidence value are provided. In alternative embodiments, only the ultrasound value or only the confidence value is determined for each voxel.

Where multiple sweeps occur, the volumes represented by each sweep are the same or overlap with other volumes. Any overlap may be compounded together. In act 38, the voxels from different sweeps are compounded together. When compounding multiple sweeps, the compounding used for combining the groups may be used (e.g., a weighted average where the weights are based on the confidence values). Alternatively, a different compounding function is used. Each sweep is independently reconstructed with the same approach (e.g., alignment and volume transformation matrix (spacing, origin, orientation)). The volumes from the sweeps are then fused in an extra post-processing step.

Further registration may be provided to further limit tracking errors and misalignment. The sweep volumes to be combined are spatially registered in three dimensions before combining. After computing the voxel overlap between each compounded sweep, the volumes are registered, such as using a sum of the square of differences to find the offset in translation and rotation in 3D space. Where more than two sweeps are provided, a volume is registered to two neighbor volumes (e.g., the volumes with maximum overlap). In one embodiment, Normalized Mutual Information with hill climbing and multiple pyramid levels is used to register. In alternative embodiments, the registration may incorporate the confidence information, such as with a confidence weighted registration. Registering single 2D frames or slabs of 2D frames to reconstructed 3D volumes or performing a brick-wise 3D registration to achieve higher performance and/or quality may be used.

In one embodiment, the intensities I(v) and confidence values C(v) at voxel v of the final compounded are computed by weighting based on the confidence values. One example representation incorporating the registration of sweep volumes is:

$$I(v) = \frac{\sum_{i \in M} C_i(R_i v) * I_i(R_i v)}{\sum_{i \in M} C_i(R_i v)}$$

$$C(v) = \max_{i \in M} C_i(R_i v)$$

where $R_i$ is the registration matrix from volume i and $I_i$, $C_i$ are its intensity and confidence values.

Figure 12:
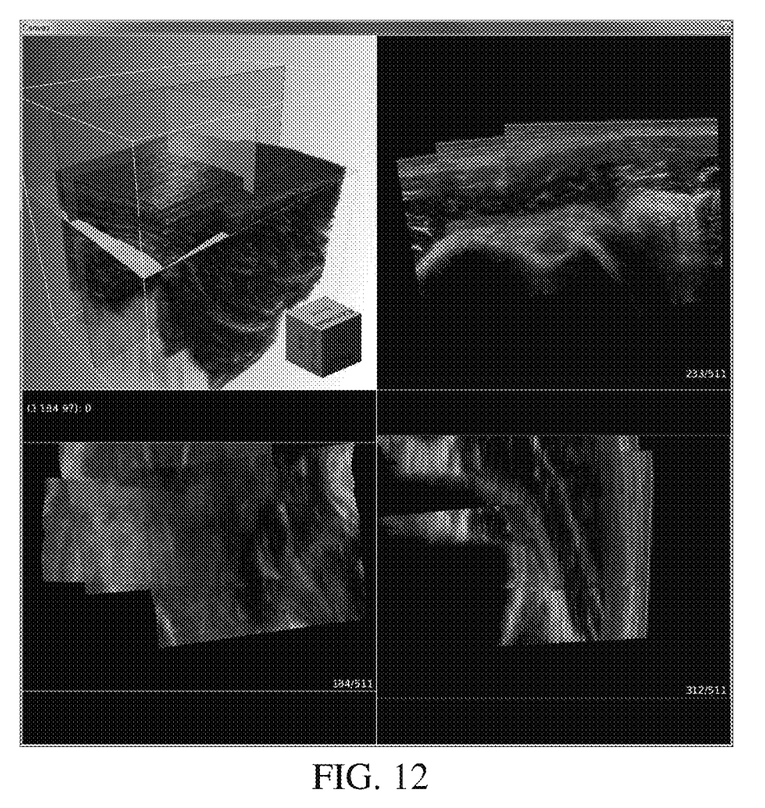
FIG. 12 shows example images generated from compounding ultrasound data from multiple sweeps.

FIG. 12 shows the results of compounding three sweeps of an arm of a patient. The transducer is moved in a first direction for the first sweep of a volume. The transducer is then reversed in direction for a second sweep of the volume. After another reversal, a third sweep is performed in the first direction, providing frames of ultrasound data representing the volume from three different sweeps. FIG. 12 shows a volume rendering of the volume subjected to the scanning from the sweeps and a multi-planar reconstruction from the volume. The multi-planar reconstruction is of three orthogonal planes shown in the volume rendering. The voxels used for rendering and multi-planar reconstruction are created by compounding from the three sweeps.

In general, two approaches for 3D spatial compounding exist. Forward compounding traverses through each pixel of each frame, computes the corresponding world coordinates, and splats the intensity into the volume's voxel structure. Backward compounding traverses the voxels of the volume and computes the set of corresponding frame pixels for each voxel. The final intensity is then determined using a weighting function. While backward compounding provides higher quality, it is also computationally more expensive due to the computation of the pixel set for each voxel and needs the whole sweep to be acquired before the volume can be reconstructed.

In one embodiment, a mixed approach is used to allow incremental compounding for real-time imaging while scanning. The compounded volume may be incrementally updated and refined. Bricking is used. To brick the volume, corners of the frames are determined relative to the volume. Bricks along scan lines are identified based on the corners.

For bricking, in a first pass, a forward sampling of each frame into a $128^3$ or other sized brick structure is performed. Each frame is sampled into an intermediate representation for each brick touched by the frame. Any intermediate representation may be used, such as storing the normal, the frame extent (e.g., 4 corners) and memory location (e.g., lookup information). As an efficient sampling, a scan line voxelization technique is used, but a brute force approach may be used, for checking each frame against each brick. Similar to scan line rasterization in computer graphics, the coordinates of the four corners of the frame are computed, a scan line axis is defined, and the corners are sorted along this axis. Exploiting the rectangularness of the frame or other frame shape, the increments or slopes along the other two axes are computed for one step along the scan line axis. Iterating brick-wise along the scan line axis, all bricks touched by the frame using simple additions are computed.

Figure 13:
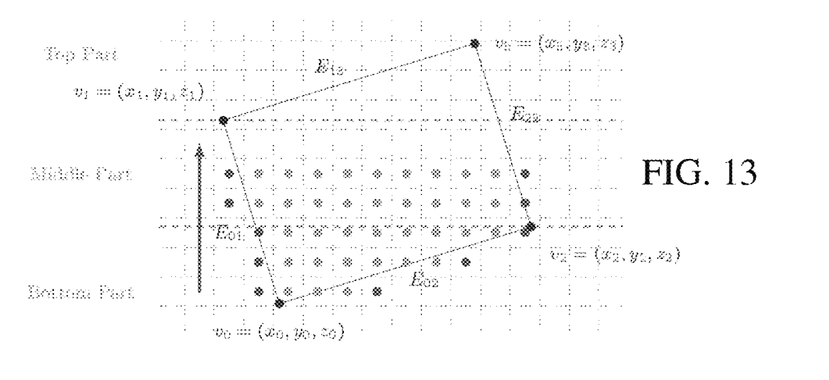
FIG. 13 illustrates one embodiment of a bricking approach for efficient compounding.

FIG. 13 illustrates the scan line voxelization scheme in 2D. Starting at the bottom-most scan line around v0, the left-most and right-most voxel covered by the ultrasound frame are computed. Using the slope of the edges E02=E13 and E01=E23, the start- and end-voxel for the next scan line are incrementally computed by simple additions. The increments are changed when advancing beyond v1 respectively to v2 (advancing to middle/top part). The created brick structure is then used to accelerate the lookup of all ultrasound frames close to a voxel for compounding.

In act 40, an image is generated using the results of the combining. The image is generated on a display by a processor or graphics processing unit. The image represents the volume of the patient. In other embodiments, the volume is segmented, clipped, filtered, or otherwise processed for imaging.

Any type of rendering may be used, such as projection or surface rendering. For projection rendering, any selection or ray line processing criteria may be used, such as maximum intensity projection. The maximum intensity along the rendering path is selected for generating a pixel of the image. Minimum, alpha blending or other projection rendering may be used. The rendering is relative to a view direction that may be established by the processor and/or the user. For any given change in view direction, the rendering paths change and the rendering process is repeated. Lighting models may be used in the rendering.

The rendering provides a two-dimensional representation of the volume of the patient. The rendering represents the scanned interior of the patient. The rendered image is displayed. The rendered image includes pixel intensities mapped to display values. The image is a two-dimensional image of the volume, including patient anatomy. Other information may be included, such as graphic overlays or image data from other modalities of imaging.

Image processing may be applied to the compounded voxels before rendering the image or applied to the rendered image. For example, the pixels representing specific structure may use a different mapping, such as color coding, to highlight the structure. As another example, spatial filtering is performed.

The image is shown alone. A sequence of such images may be shown, such as rendering from a sequence of different view directions or rendering while acquiring further scan data. Alternatively, the image or images are shown with other information. The image may be separate but share the display screen with an image generated from another imaging modality. In alternative or additional embodiments, the compounded data is used for quantification. A volume, area, length, curvature, or other quantity is calculated using the voxel values. Quantities may be calculated on derived images (e.g., strain, harmonic, or other scalar quantity). Since the sweep may be on any arbitrary surface, the sweep is reformatted so that a measurement between two points is the actual geodesic distance. Measurements only on part (user defined or automatic) of the region (e.g., average intensity inside a ellipsoid) may be provided.

In one embodiment, a representation of the volume is displayed as one or more two-dimensional (e.g., 3D renderings, volume cross sections) images on the display. The displayed images may be arbitrary reformats of the volume. The reformatting restores the curved swept surface of the skin or physical structure to a plane or the curved path to a straight line. A user interface allows the user to interact with the display to perform quantitative measurements of volume, area, length, average intensity, intensity profile or other measurement. The user may define any measurement, such as selecting an arbitrary group of voxels. The processor or user may classify different voxels or pixels as belonging to different categories (e.g., types of tissue or lesion). The measurements may be made specific to the category.

In an alternative or additional embodiment, an image is generated from the confidence information. Using just the confidence values for each voxel or using the confidence values and ultrasound values, the image is generated and displayed. For using both, the confidence values may be used to modulate a color, brightness or other display characteristic. For using confidence values alone, the confidence values prior to rendering or the resulting pixels after rendering are mapped to display values. As discussed above, a maximum confidence value is selected for each voxel as part of compounding. By displaying an image rendered from the maximum confidence values associated with each pixel and/or voxel, regions of the volume associated with lesser confidence may be identified by the user. The user then moves the transducer to acquire ultrasound values for that region to incrementally compound with the more uncertain values previously obtained. This confidence information is exposed to the clinician in order to assist the clinician in determining regions that need further examination for a complete reconstruction.

Figure 14:
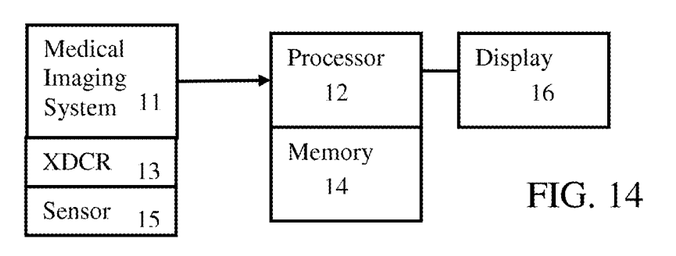
FIG. 14 is a block diagram of one embodiment of a system for 3D ultrasound imaging.

FIG. 14 shows a system for three-dimensional ultrasound imaging. The system includes a medical imaging system 11, a transducer 13, a sensor 15, a processor 12, a memory 14, and a display 16. The processor 12 and the memory 14 are shown separate from the medical imaging system 11, such associated with being a computer or workstation apart from the medical imaging system 11. In other embodiments, the processor 12 and/or memory 14 are part of the medical imaging system 11. In alternative embodiments, the system is a workstation, computer, or server for three-dimensional ultrasound imaging from data acquired by a separate system in real-time or using previously acquired patient-specific data stored in the memory 14. For example, the medical imaging system 11 is provided for acquiring data representing a volume, and a separate database, server, workstation, and/or computer is provided for three-dimensional imaging. Additional, different, or fewer components may be used. Other sensors may be provided, such as for tracking position and/or orientation of the patient.

The computing components of the system, such as the medical imaging system 11 and/or the processor 12 are configured by hardware, software, and/or circuit design to perform calculations or other acts. The computing components operate independently or in conjunction with each other to perform any given act. The act is performed by one of the computer components, another of the computing components, or a combination of the computing components. Other components may be used by the computing components to scan or perform other functions.

The transducer 13 is an array, such as a one dimensional, two dimensional, or multi-dimensional array of elements. The elements are piezoelectric or capacitive membrane ultrasound transducer elements. Any now known or later developed array may be used.

The transducer 13 includes a probe housing in which the array is located. The probe housing is sized and shaped for handheld use by the clinician. The clinician grips the probe housing and moves the transducer 13 over the patient during scanning.

The sensor 15 connects with or is separate from the transducer 13. For example, the sensor 15 is a magnetic position sensor with antennas in the transducer 13 as well as antennas spaced from the transducer 13. In another example, the sensor 15 is an optical sensor, such as a camera spaced from the transducer 13. A processor processes images from the optical sensor to determine the position and orientation of the transducer 13.

The ultrasound system 11 is a cart based, handheld, computer-based, or other now known or later developed ultrasound system 11 for scanning a patient. The ultrasound system 11 includes a transmit beamformer for forming acoustic beams, a receive beamformer for sampling acoustic response to the transmit beams, and a detector (e.g., B-mode intensity, harmonic mode, contrast mode, power Doppler, or other). Additional components may be provided, such as an image processor, filter, scan converter, or graphics processing unit. Any now known or later developed ultrasound system 11 for scanning a volume of a patient may be used.

The ultrasound system 11 connects through a wire or wirelessly with the transducer 13 for scanning in three dimensions. As the transducer 13 is moved or swept, the ultrasound system 11 acquires data representing locations in different planes throughout a volume of the patient. Some data may represent the same locations. Some planes may be at different orientations due to rotation of the transducer and/or curvature of the skin surface.

The processor 12 is a general processor, digital signal processor, three-dimensional data processor, graphics processing unit, application specific integrated circuit, field programmable gate array, digital circuit, analog circuit, combinations thereof, or other now known or later developed device for processing medical data. The processor 12 is a single device, a plurality of devices, or a network. For more than one device, parallel or sequential division of processing may be used. Different devices making up the processor 12 may perform different functions, such as creating the curved reformation sub-volume by one processor and rendering by another processor. In one embodiment, the processor 12 is a control processor or other processor of the medical imaging system 11. The processor 12 operates pursuant to stored instructions to perform various acts described herein, such as acts of FIG. 1.

The processor 12 is configured to label ultrasound values in the frames with indications of reliability, such as assigning confidence or uncertainty values based on scan format and/or detected structure represented in the frame. Lookup, filtering, or classification is used to label the ultrasound values for the locations. For each frame, indications are provided for each of the ultrasound values for the different locations.

The processor 12 is configured to spatially align the frames of data relative to the scanned volume. Any registration or transformation may be used. The processor 12 determines which locations represented in which frames correspond to the same voxels or vise versa. Registration may avoid alignment errors. Any of the registrations discussed herein may be used.

The processor 12 is configured to combine different data representing the same locations. Data representing the same voxels or planar locations but in different frames are combined. One, two, or more sequential combinations may be provided for a given voxel or location, such as separating the frames into groups, combining common locations in the groups, combining common locations between the groups, and combining the resulting volumes for a sweep with other volumes for a different sweep.

The combination is a function of the indications of reliability. The indications may be used to weight for weighted averaging. The processor 12 provides a stronger influence of reliable ultrasound values in combining the values for a location. The indications may be used in one or more of sequential compounding acts. For example, frames are grouped by orientation. In compounding the frames within an orientation group, the indications are used for weighting. When compounding groups together, the indications are used for weighting. When compounding sweeps together, the indications are used for weighting. The indications may not be used in other embodiments for one or more of the sequential compounding operations.

The processor 12 is configured to render an image from the compounded ultrasound values and/or the confidence values. The processor 12 is configured to generate an image. The image is generated as a projection or surface rendering. The image is a volume or three-dimensional rendering or other reconstruction.

The display 16 is a CRT, LCD, plasma, projector, printer, or other output device for showing an image. The display 16 displays an image of the volume of the patient. A measure based on the scanned volume, such as a distance, may be displayed in a chart, graph, and/or on an image. The image may include other information, such as an overlay or color coding from the indications.

The memory 14 is a buffer, cache, RAM, removable media, hard drive, magnetic, optical, database, or other now known or later developed memory. The memory 14 is a single device or group of two or more devices. The memory 14 is within the system 11, part of a computer with the processor 12, or is outside or remote from other components.

The memory 14 stores the data representing the patient, weights, registrations, matrices, transforms, voxels, and/or compounding information. The data represents different planes in a volume and may be from one or more sweeps of the volume with the transducer 13. The data represents a three-dimensional region. Any format may be used, such as voxels interpolated to a three-dimensional grid or data representing parallel or non-parallel planes. The data may be segmented, such as including locations known to be for different anatomy.

The memory 14 is additionally or alternatively a non-transitory computer readable storage medium with processing instructions. The memory 14 stores data representing instructions executable by the programmed processor 12 for three-dimensional ultrasound imaging. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for three-dimensional ultrasound imaging, the method comprising:
    acquiring, with an ultrasound system including a transducer, first and second ultrasound data representing a same volume of a patient, at least some of the first ultrasound data representing the same locations as at least some of the second ultrasound data;
    assigning, by a processor, confidence values as a function of location within the volume to the first and second ultrasound data;
    combining, by the processor and for each of the same locations, the first and second ultrasound data representing each of the same locations within the volume, the combining being a function of the confidence values for the locations; and
    generating an image on a display using results of the combining, the image representing the volume of the patient.

2. The method of claim 1 wherein acquiring comprises acquiring with free hand motion of the transducer, the first and second ultrasound data being from first and second sweeps of the transducer in different directions.

3. The method of claim 1 wherein acquiring comprises acquiring with the transducer along a curved skin surface, the first and second ultrasound data being for frames along planes at different angles relative to the volume due to the curved skin surface.

4. The method of claim 1 wherein assigning comprises assigning the confidence values as a function of scan format and depth.

5. The method of claim 1 wherein assigning comprises assigning the confidence values as a function of structure detected in the volume.

6. The method of claim 1 further comprising transforming the locations from planes into three-dimensional space as a function of signals from a sensor on the transducer.

7. The method of claim 6 further comprising low pass filtering the signals from the sensor, a kernel size of the low pass filtering being a function of a density of the planes.

8. The method of claim 1 further comprising spatially registering frames of the first ultrasound data, the second ultrasound data, or the first and second ultrasound data.

9. The method of claim 8 wherein spatially registering comprises spatially registering patches and generating a depth-based deformation field as a function of results of the spatially registering of the patches.

10. The method of claim 1 wherein combining comprises interpolating with weights that are a function of the confidence values and distance to voxel centers.

11. The method of claim 1 wherein combining comprises weighting the first ultrasound data with confidence values for the first ultrasound data, weighting the second ultrasound data with confidence values for the second ultrasound data, summing results of the weighting for each location, and dividing the summed results by a sum of the confidence values for the first and second ultrasound data.

12. The method of claim 1 further comprising registering the first ultrasound data with the second ultrasound data in three-dimensional space, and wherein combining comprises combining as a function of the registering in the three-dimensional space.

13. The method of claim 1 further comprising selecting a maximum confidence for each location and generating a confidence image as a function of the maximum confidences.

14. The method of claim 1 further comprising:
    determining corners represented by the frames of the first ultrasound data relative to the volume, the frames representing planes of the volume; and
    identifying bricks of sub-volumes of the first ultrasound data along a scan line based on the corners;
    wherein combining comprises combining using the identified bricks.

15. The method of claim 1 where the first and second ultrasound data comprise tissue strain, power Doppler, contrast agent, tissue harmonics, elastic modulus, relaxation time or other tissue property.

16. The method of claim 1 further comprising:
    providing a user interface to interact with the display to perform quantitative measurements of volume, area, length, average intensity, intensity profile;
    reformatting a curved surface or path to straight; and
    calculating a quantity as a function of the reformatted curved surface or path in response to the user interface.

* * * * *